(12) United States Patent
Bedingham et al.

(10) Patent No.: US 7,709,249 B2
(45) Date of Patent: *May 4, 2010

(54) MULTIPLEX FLUORESCENCE DETECTION DEVICE HAVING FIBER BUNDLE COUPLING MULTIPLE OPTICAL MODULES TO A COMMON DETECTOR

(75) Inventors: William Bedingham, Woodbury, MN (US); Peter D. Ludowise, Cottage Grove, MN (US); Barry W. Robole, Woodville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 1297 days.

This patent is subject to a terminal disclaimer.

(21) Appl. No.: 11/174,755

(22) Filed: Jul. 5, 2005

(65) Prior Publication Data

US 2006/0223172 A1  Oct. 5, 2006

Related U.S. Application Data

(60) Provisional application No. 60/667,461, filed on Apr. 1, 2005.

(51) Int. Cl.
C12M 1/34 (2006.01)
C12M 3/00 (2006.01)
(52) U.S. Cl. .................................................. 435/288.7
(58) Field of Classification Search ............... 435/288.7
See application file for complete search history.

(56) References Cited

U.S. PATENT DOCUMENTS

| 3,918,793 A | 11/1975 | Kraaft ........................... 350/91 |
| 3,949,231 A | 4/1976 | Blunck et al. ................. 250/493 |
| 4,343,991 A | 8/1982 | Fujiwara et al. .............. 250/227 |
| 4,726,676 A | 2/1988 | Maslaney et al. |
| 4,909,990 A | 3/1990 | Block et al. ............... 422/82.11 |
| 4,927,766 A | 5/1990 | Auerbach et al. ............. 436/44 |

(Continued)

FOREIGN PATENT DOCUMENTS

CN  1311436 A  9/2001

(Continued)

OTHER PUBLICATIONS

Wenner et al.; "Biosensing on the CD Microfluidic Platform with Genetically Engineered Proteins"; Society of Automotive Engineers, Inc.; Paper 2000-01-2513; pp. 1-6; 2000.

(Continued)

*Primary Examiner*—Walter D Griffin
*Assistant Examiner*—Lydia Edwards

(57) ABSTRACT

Techniques are described for the detection of multiple target species in real-time PCR (polymerase chain reaction). For example, a system is described that includes a data acquisition device and a detection device coupled to the data acquisition device. The detection device includes a rotating disk having a plurality of process chambers having a plurality of species that emit fluorescent light at different wavelengths. The device further includes a plurality of optical modules. Each of the optical modules is optically configured to excite the species and capture fluorescent light emitted by the species at different wavelengths. A fiber optic bundle coupled to the plurality of optical modules conveys the fluorescent light from the multiple optical modules to a single detector.

29 Claims, 12 Drawing Sheets

U.S. PATENT DOCUMENTS

| | | | |
|---|---|---|---|
| 5,296,958 A | 3/1994 | Roddy et al. | |
| 5,414,600 A | 5/1995 | Strobl et al. | 362/32 |
| 5,473,437 A | 12/1995 | Blumenfeld et al. | 356/417 |
| 5,585,069 A | 12/1996 | Zanzucchi et al. | 422/100 |
| 5,639,668 A | 6/1997 | Neel et al. | 436/172 |
| 5,751,874 A | 5/1998 | Chudoba et al. | |
| 5,766,889 A | 6/1998 | Atwood | 435/91.2 |
| 5,928,907 A | 7/1999 | Woudenberg et al. | 435/91.2 |
| 5,994,150 A | 11/1999 | Challener et al. | 436/518 |
| 6,015,674 A | 1/2000 | Woudenberg et al. | 435/6 |
| 6,144,448 A | 11/2000 | Mitoma | 356/317 |
| 6,161,946 A | 12/2000 | Bishop et al. | |
| 6,232,075 B1 | 5/2001 | Williams | |
| 6,339,473 B1 | 1/2002 | Gordon | 356/440 |
| 6,342,349 B1 | 1/2002 | Virtanen | 435/6 |
| 6,442,116 B2 | 8/2002 | Asano | |
| 6,537,211 B1 | 3/2003 | Wang et al. | |
| 6,563,113 B1 | 5/2003 | Amann et al. | |
| 6,563,581 B1 | 5/2003 | Oldham et al. | 356/317 |
| 6,597,450 B1 | 7/2003 | Andrews et al. | 356/317 |
| 6,597,832 B2 | 7/2003 | Cheng | |
| 6,616,304 B2 | 9/2003 | Li | 362/302 |
| 6,627,159 B1 | 9/2003 | Bedingham et al. | 422/100 |
| 6,734,401 B2 | 5/2004 | Bedingham et al. | 219/388 |
| 6,803,999 B1 | 10/2004 | Gordon | 356/73 |
| 6,806,954 B2 | 10/2004 | Sandstrom | 356/317 |
| 6,821,771 B2 | 11/2004 | Festoc | 435/287 |
| 6,833,536 B2 | 12/2004 | Shigeura | 219/553 |
| 6,992,278 B2 | 1/2006 | Sjoberg et al. | 250/231 |
| 6,992,769 B2 | 1/2006 | Gordon | 356/440 |
| 7,088,650 B1 | 8/2006 | Worthington et al. | |
| 7,238,269 B2 | 7/2007 | Gason et al. | |
| 7,322,254 B2 | 1/2008 | Bedingham et al. | |
| 7,507,575 B2 * | 3/2009 | Bedingham et al. | 435/287.2 |
| 2001/0029036 A1 | 10/2001 | Landers et al. | 435/91.1 |
| 2001/0046712 A1 | 11/2001 | Hang et al. | |
| 2001/0052927 A1 | 12/2001 | Takase et al. | |
| 2002/0039333 A1 | 4/2002 | Tsukahara et al. | |
| 2002/0043626 A1 | 4/2002 | Booker et al. | 250/459 |
| 2002/0047003 A1 | 4/2002 | Bedingham et al. | |
| 2002/0048533 A1 | 4/2002 | Harms et al. | 422/99 |
| 2002/0064885 A1 | 5/2002 | Bedingham et al. | 436/174 |
| 2002/0076354 A1 | 6/2002 | Cohen | 422/72 |
| 2002/0104884 A1 | 8/2002 | Meier et al. | |
| 2002/0172980 A1 | 11/2002 | Phan et al. | |
| 2003/0054563 A1 | 3/2003 | Ljungstrom et al. | 436/172 |
| 2003/0124506 A1 | 7/2003 | Bedingham et al. | 435/4 |
| 2003/0190184 A1 | 10/2003 | O'Brien et al. | |
| 2003/0219754 A1 | 11/2003 | Oleksy et al. | 435/6 |
| 2004/0067051 A1 | 4/2004 | Kylberg et al. | 392/407 |
| 2004/0072335 A1 | 4/2004 | Boege et al. | 435/287 |
| 2004/0126279 A1 | 7/2004 | Renzi et al. | |
| 2004/0224317 A1 | 11/2004 | Kordunsky et al. | 435/6 |
| 2005/0012199 A1 | 1/2005 | Rosenau et al. | |
| 2005/0014249 A1 | 1/2005 | Staimer et al. | 435/287 |
| 2005/0023765 A1 | 2/2005 | Coombs | 277/345 |
| 2005/0048595 A1 | 3/2005 | Yamatsu et al. | 435/18 |
| 2005/0059062 A1 | 3/2005 | Kaiser | 435/6 |
| 2005/0064582 A1 | 3/2005 | Wittwer et al. | 435/287 |
| 2005/0074784 A1 | 4/2005 | Vo-Dinh | 435/6 |
| 2005/0109396 A1 | 5/2005 | Zucchelli et al. | 137/67 |
| 2005/0130177 A1 | 6/2005 | Bedingham et al. | 435/6 |
| 2005/0151972 A1 | 7/2005 | Boege et al. | 356/417 |
| 2006/0223169 A1 | 10/2006 | Bedingham et al. | 435/287 |
| 2006/0223172 A1 | 10/2006 | Bedingham et al. | 435/288 |
| 2007/0009382 A1 | 1/2007 | Bedingham et al. | 422/63 |
| 2007/0009383 A1 | 1/2007 | Bedingham et al. | 422/63 |
| 2007/0010007 A1 | 1/2007 | Aysta et al. | 435/287 |

FOREIGN PATENT DOCUMENTS

| | | |
|---|---|---|
| CN | 1354361 A | 6/2002 |
| CN | 2522854 Y | 11/2002 |
| CN | 1262833 C | 7/2006 |
| DE | 2 055 944 | 5/1972 |
| GB | 1 599 452 | 10/1981 |
| JP | 61-20839 | 1/1986 |
| WO | WO 91/03915 | 3/1991 |
| WO | WO 98/38510 | 9/1998 |
| WO | WO 01/01112 | 1/2001 |
| WO | WO 01/65242 | 9/2001 |
| WO | WO 02/073605 | 9/2002 |
| WO | WO 03/058253 | 7/2003 |
| WO | WO 03/098278 | 11/2003 |
| WO | WO 03/098279 | 11/2003 |
| WO | WO 03/102226 | 12/2003 |
| WO | WO 2004/079343 | 9/2004 |
| WO | WO 2004/087950 | 10/2004 |

OTHER PUBLICATIONS

Lee et al.; "A novel real-time PCR machine with a miniature spectrometer for fluorescence sensing in a micro liter volume glass capillary"; Sensors and Actuators B 100 (2004) 401-410.

Lee et al.; "Development of a CCD-based fluorimeter for real-time PCR machine"; Sensors and Actuators B 107 (2005) 872-881.

Office Action from U.S. Appl. No. 11/174,754 dated Jan. 2, 2008.

* cited by examiner

MULTIPLEX FLUORESCENCE DETECTION DEVICE HAVING FIBER BUNDLE COUPLING MULTIPLE OPTICAL MODULES TO A COMMON DETECTOR

CROSS REFERENCE TO RELATED APPLICATIONS

This application claims the benefit of U.S. Provisional Application No. 60/667,461, filed Apr. 1, 2005, the entire content of which is incorporated herein by reference.

TECHNICAL FIELD

The invention relates to assaying systems and, more particularly, techniques for the detection of multiple target species using fluorescent dyes.

BACKGROUND

Optical disc systems are often used to perform various biological, chemical or bio-chemical assays. In a typical system, a rotatable disc is used as a medium for storing and processing fluid specimens, such as blood, plasma, serum, urine or other fluid.

One type of analysis is polymerase chain reaction (PCR), which is often used for nucleic acid sequence analysis. In particular, PCR is often used for DNA sequencing, cloning, genetic mapping, and other forms of nucleic acid sequence analysis.

In general, PCR relies on the ability of DNA-copying enzymes to remain stable at high temperatures. There are three major steps in PCR: denaturation, annealing, and extension. During the denaturation, a liquid sample is heated at approximately 94° C. During this process, double-stranded DNA "melts" open into single-stranded DNA. During annealing, the single-stranded DNA is cooled to approximately 54° C. At this temperature, primers bind or "anneal" to the ends of the DNA segments that are to be replicated. During extension, the sample is heated to 75° C. At this temperature, enzymes add nucleotides add to the target sequence and eventually a complementary copy of the DNA template is formed. The new DNA strand becomes a new target for the next sequence of events, or "cycle."

There are a number of existing PCR instruments designed to determine levels of specific DNA and RNA sequences in the sample during the PCR in real-time. Many of the instruments are based on the use of fluorescent dyes. In particular, many conventional real-time PCR instruments detect a fluorescent signal produced proportionally during amplification of a PCR product.

Conventional real-time PCR instruments use different methods for detection of different fluorescent dyes. For example, some conventional PCR instruments incorporate white light sources with filter wheels for spectrally resolving each dye. The white light sources are tungsten halogen bulbs, which have a lifetime maxima of a few thousand hours. The filter wheels are typically complicated electromechanical parts that are susceptible to wear.

SUMMARY

In general, the invention relates to techniques for the detection of multiple target species in real-time PCR (polymerase chain reaction), referred to herein as multiplex PCR. In particular, a multiplex fluorescence detection device is described that incorporates a plurality of optical modules. Each of the optical modules may be optimized for detection of a respective fluorescent dye at a discrete wavelength band. In other words, the optical modules may be used to interrogate multiple, parallel reactions at different wavelengths. The reaction may, for example, occur within a single process chamber (e.g., well) of a rotating disk.

The plurality of optical modules are optically coupled to a single detector by a multi-legged optical fiber bundle. In this manner, multiplexing is achieved by using a plurality of optical modules and a single detector, e.g., a photomultiplier tube. The optical components in each optical module may be selected to maximize sensitivity and minimize the amount of spectral crosstalk, i.e., signals from one dye on another optical module.

In one embodiment, a device comprises a rotating disk having a plurality of process chambers holding a respective sample and a plurality of fluorescent dyes. The device further includes a plurality of optical modules, each of the optical modules includes a light source selected for a different one of the dyes. The light sources of the optical modules excite different regions of the rotating disk and capture fluorescent light emitted from the disk. A fiber optic bundle is coupled to the plurality of optical modules to convey the fluorescent light from the multiple optical modules to a single detector.

In another embodiment, a system comprises a data acquisition device. The system further comprises a detection device coupled to the data acquisition device, wherein the detection device comprises a rotating disk having a plurality of process chambers each having a plurality of species that emit fluorescent light at different wavelengths, a plurality of optical modules, wherein each of the optical modules is optically configured to excite the species and capture fluorescent light emitted by the species at different wavelengths, a detector, and a fiber optic bundle coupled to the plurality of optical modules to convey the fluorescent light from the multiple optical modules to the detector.

In an additional embodiment, a method comprises rotating a disk having a plurality of process chambers each having a plurality of species that emit fluorescent light at different wavelengths; exciting the disk with a plurality of light beams to produce a plurality of emitted fluorescent light beams; capturing the fluorescent light beams with a plurality of different optical modules, wherein the optical modules are optically configured for the different wavelengths; conveying the fluorescent light beams from the plurality of optical modules to a single detector with a fiber optic bundle; and outputting a signal from the detector representative of the fluorescent light beams.

While the device may be capable of conducting real-time PCR, the device may be capable of analyzing any type of biological reaction while it occurs. The device may be able to modulate the temperature of each reaction independently or as a selected group, and the device may be able to support multiple stages of reactions by including a valve between two chambers. This valve may be opened during reactions through the use of a laser which delivers a burst of energy to the valve.

In some embodiments, the device may be portable to allow operation in remote areas or temporary laboratories. The device may include a data acquisition computer for analyzing the reactions in real-time, or the device may communicate the data to another device through wired or wireless communication interfaces.

The details of one or more embodiments of the invention are set forth in the accompanying drawings and the descrip-

DETAILED DESCRIPTION

Figure 1:
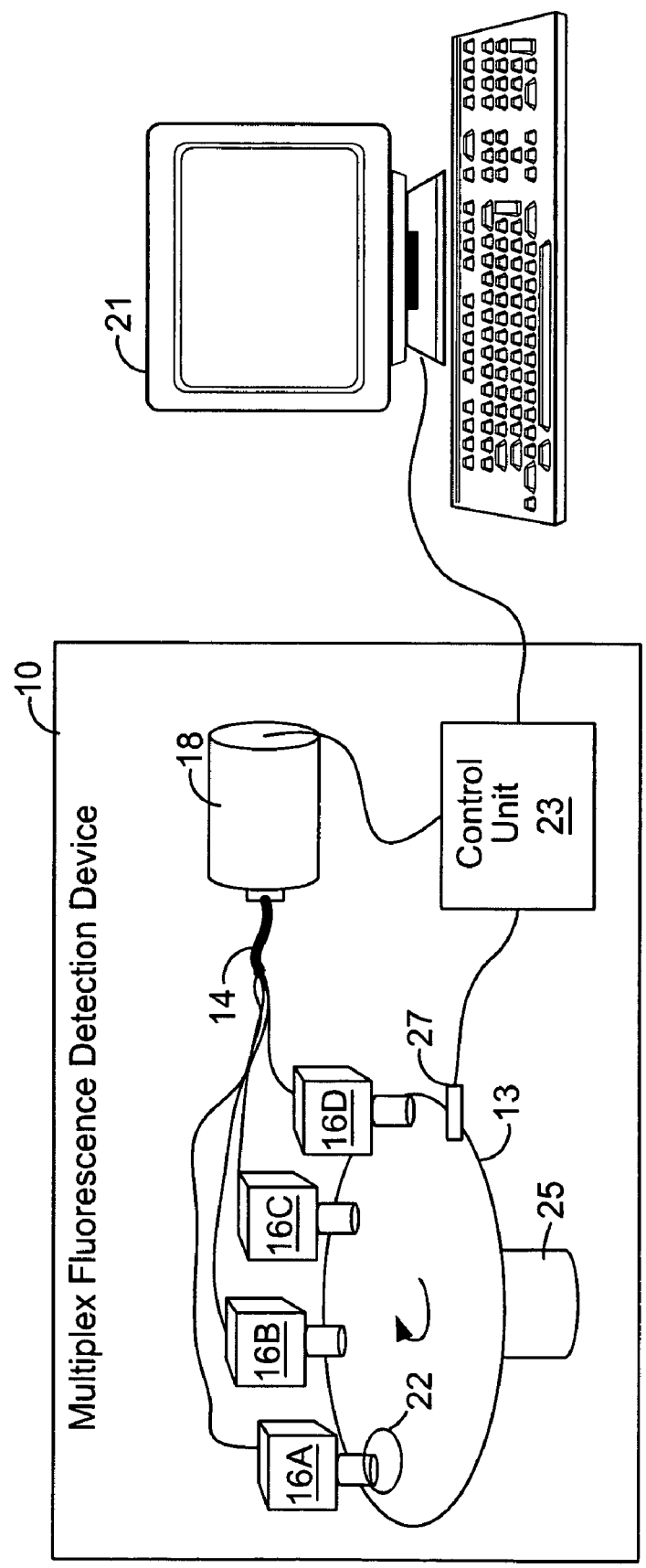
FIG. 1 is a block diagram illustrating an exemplary embodiment of a multiplex fluorescence detection device.

FIG. 1 is a block diagram illustrating an exemplary embodiment of a multiplex fluorescence detection device 10. In the illustrated example, device 10 has four optical modules 16 that provide four "channels" for optical detection of four different dyes. In particular, device 10 has four optical modules 16 that excite different regions of rotating disk 13 at any given time, and collect emitted fluorescent light energy at different wavelengths from the dyes. As a result, optical modules 16 may be used to interrogate multiple, parallel reactions occurring within sample 22.

The multiple reactions may, for example, occur simultaneously within a single chamber of a rotating disk 13. Each of optical modules 16 interrogates sample 22 and collects fluorescent light energy at different wavelengths as the disk 13 rotates. For example, excitation sources within modules 16 may be sequentially activated for periods sufficient to collect data at the corresponding wavelengths. That is, an optical module 16A may be activated for a period of time to collect data at a first range of wavelengths selected for a first dye corresponding to a first reaction. The excitation source may then be deactivated, and an excitation source within module 16B may be activated to interrogate sample 22 at a second range of wavelengths selected for a second dye corresponding to a second reaction. This process continues until data has been captured from all optical modules 16. In one embodiment, each of the excitation sources within optical modules 16 is activated for an initial period of approximately two seconds to reach steady state followed by an interrogation period which lasts for 10-50 rotations of disk 13. In other embodiments, the excitation sources may be sequenced for shorter (e.g., 1 or 2 milliseconds) or longer periods. In some embodiments, more than one optical module may be activated simultaneously for concurrent interrogation of sample 22 while disk 13 rotates.

Although a single sample 22 is illustrated, disk 13 may contain a plurality of chambers holding samples. Optical modules 16 may interrogate some or all of the different chambers at different wavelengths. In one embodiment, disk 13 includes 96 chambers space around a circumference of disk 13. With a 96 chamber disk and four optical modules 16, device 10 may be capable of acquiring data from 384 different species.

In one embodiment, optical modules 16 include excitation sources that are inexpensive high power light emitting diodes (LEDs), which are commercially available in a variety of wavelengths and have long lifetimes (e.g., 100,000 hours or more). In another embodiment, conventional halogen bulbs or mercury lamps may be used as excitation sources.

As illustrated in FIG. 1, each of optical modules 16 may be coupled to one leg of a fiber optic bundle 14. Fiber optic bundle 14 provides a flexible mechanism for collection of fluorescent signals from optical modules 16 without loss of sensitivity. In general, a fiber optic bundle comprises multiple optical fibers laid side by side and bonded together at the ends and encased in a flexible protective jacket. Alternatively, fiber optic bundle 14 may comprise a smaller number of discrete, large diameter multi-mode fibers, either glass or plastic, having a common end. For example, for a four-optical module device, fiber optic bundle 16 may comprise four discrete multimode fibers, each having a 1 mm core diameter. The common end of the bundle contains the four fibers bound together. In this example, the aperture of detector 18 may be 8 mm, which is more than sufficient for coupling to the four fibers.

In this example, fiber optic bundle 14 couples optical modules 16 to a single detector 18. The optical fibers carry the fluorescent light collected by optical modules 16 and effectively deliver the captured light to detector 18. In one embodiment, detector 18 is a photomultiplier tube. In another embodiment, the detector may include multiple photomultiplier elements, one for each optical fiber, within the single detector. In other embodiments, one or more solid-state detectors may be used.

The use of a single detector 18 may be advantageous in that it allows use of a highly sensitive and possibly expensive detector (e.g., a photomultiplier), while maintaining a minimal cost in that only a single detector need be used. A single detector is discussed herein; however, one or more detectors may be included for detecting a greater number of dyes. For example, four additional optical modules 16 and a second detector may be added to the system to allow for the detection of eight different wavelengths emitted from one disk.

Optical modules 16 are removable from the device and easily interchangeable with other optical modules that are optimized for interrogation at different wavelengths. For example, optical modules 16 may be physically mounted within locations of a housing. Each of optical modules 16 may be easily inserted within a respective location of the housing along guides (e.g., recessed grooves) that mate with one or more marking (e.g., guide pins) of the optical module. Each optical module includes an optical output port (shown in FIG. 2) for coupling to one leg of fiber optic bundle 14. The optical output port may have a threaded end coupled to a threaded connector of the leg. Alternatively, a form of "quick-connect" may be used (e.g., a slidable connection having an o-ring and a catch pin) that allows fiber optic bundle 14 to be slidably engaged and disengaged from the optical output port. Moreover, each of optical modules 16 may have one or more electrical contacts for electronically coupling to control unit 23 when fully inserted. Exemplary removable optical modules for use with rotating disk 13 are described in U.S. patent application Ser. No. 11/174,754, entitled "MULTIPLEX FLUORESCENCE DETECTION DEVICE HAVING REMOVABLE OPTICAL MODULES," filed on Jul. 5, 2005, the entire content of which is hereby incorporated by reference.

The modular architecture of device 10 allows the device to be easily adapted for all of the fluorescent dyes used in a given analysis environment, such as multiplex PCR. Other chemistries that may be used in device 10 include Invader (Third Wave, Madison, Wis.), Transcripted-mediated Amplification (GenProbe, San Diego, Calif.), fluorescence labeled enzyme linked immunosorbent assay (ELISA) or fluorescence in situ hybridization (FISH). The modular architecture of device 10 may provide another advantage in that the sensitivity of each optical module 16 can be optimized by choice of the corresponding excitation source (not shown) and excitation and detection filters for a small specific target range of wavelengths in order to selectively excite and detect a corresponding dye in the multiplex reaction.

For purpose of example, device 10 is illustrated in a 4-color multiplex arrangement, but more or less channels can be used with the appropriate fiber optic bundle 14. This modular design allows a user to easily upgrade device 10 in the field by simply adding another optical module 16 to base 20 and inserting one leg of fiber optic bundle 14 into the new optical module. Optical modules 16 may have integrated electronics that identify the optical modules and download calibration data into an internal control optical module or other internal electronics (e.g., control unit 23) of device 10.

In the example of FIG. 1, samples 22 are contained in chambers of disk 13, which is mounted on a rotating platform under the control of control unit 23. A slot sensor trigger 27 provides an output signal utilized by control unit 23 and data acquisition for synchronizing data acquisition with chamber position during disk rotation. Slot sensor trigger 27 may be a mechanical or optical sensor. For example, the sensor may be a laser which sends a beam of light to disk 13, and control unit 23 uses a sensor detecting light passing through a slot in disk 13 to locate the chambers on the disk. Optical modules 16 may be physically mounted above rotating platform 25. As a result, optical modules 16 are overlapped with different chambers at any one time.

Detection device 10 also includes a heating element (not shown) for modulating the temperature of the sample 22 on disk 13. The heating element may comprise a cylindrical halogen bulb contained within a reflective enclosure. The reflective chamber is shaped to focus radiation from the bulb onto a radial section of disk 13. Generally, the heated area of disk 13 would resemble a ring as disk 13 spins. In this embodiment, the shape of the reflective enclosure may be a combination of elliptical and spherical geometries that allow precise focusing. In other embodiments, the reflective enclosure may be of a different shape or the bulb may broadly irradiate a larger area. In other embodiments, the reflective enclosure may be shaped to focus the radiation from the bulb onto a single area of the disk 13, such as a single process chamber containing a sample 22.

In some embodiments, the heating element may heat air and force the hot air over one or more samples to modulate the temperature. Additionally, the samples may be heated directly by the disk. In this case, the heating element may be located in platform 25 and thermally couple to disk 13. Electrical resistance within the heating element may heat a selected region of the disk as controlled by control unit 23. For example, a region may contain one or more chambers, possibly the entire disk. An exemplary heating element for use with rotating disk 13 is described in U.S. patent application Ser. No. 11/174,691, entitled "HEATING ELEMENT FOR A ROTATING MULTIPLEX FLUORESCENCE DETECTION DEVICE," filed on Jul. 5, 2005, the entire content of which is hereby incorporated by reference.

Alternatively, or in addition, device 10 may also includes a cooling component (not shown). A fan is included in device 10 to supply cold air, i.e., room temperature air, to disk 13. Cooling may be needed to modulate the temperature of the sample appropriately and store samples after an experiment has completed. In other embodiments, the cooling component may include thermal coupling between platform 25 and disk 13, as platform 25 may reduce its temperature when needed. For example, some biological samples may be stored at 4 degrees Celsius to reduce enzyme activity or protein denaturing.

Detection device 10 may also be capable of controlling reaction species contained within a process chamber. For example, it may be beneficial to load some species in a process chamber to generate one reaction and later adding another species to the sample once the first reaction has terminated. A laser homing valve system may be added to control a valve separating an inner holding chamber from the process chamber, thereby controlling the addition of species to the chamber during rotation of disk 13. This laser homing valve system may be located within one of optical modules 16 or separate from the optical modules. Directly below the laser, under disk 13, may be a laser sensor for positioning the laser relative to disk 13.

In one embodiment, the laser is a near infrared (NIR) laser with at least two power settings. Under a low power setting, the laser positioning sensor may indicate that the laser is in position over the chamber valve by recognizing the NIR light though a slot in disk 13. Once the laser is in position, control unit 23 directs the laser to output a short burst of high power energy to heat the valve and open it. The open valve may then allow the inner fluid specimen to flow toward from the inside chamber to the outside process chamber and conduct a second reaction. In some embodiments, disk 13 may contain a plurality of valves to generate a plurality of reactions in sequence. More than one set of laser and laser sensor may also be used when utilizing multiple chamber valves. An exemplary laser homing valve control system for use with rotating disk 13 is described in U.S. patent application Ser. No. 11/174,957, entitled "VALVE CONTROL SYSTEM FOR A ROTATING MULTIPLEX FLUORESCENCE DETECTION DEVICE," filed on Jul. 5, 2005, the entire content of which is hereby incorporated by reference.

Data acquisition system 21 may collect data from device 10 for each dye either sequentially or in parallel. In one embodiment, data acquisition system 21 collects the data from optical modules 16 in sequence, and corrects the spatial overlap by a trigger delay for each one of the optical modules measured from slot sensor trigger 27.

One application for device 10 is real-time PCR, but the techniques described herein may be extended to other platforms that utilize fluorescence detection at multiple wavelengths. Device 10 may combine rapid thermal cycling, utilizing the heating element, and centrifugally driven microfluidics for isolation, amplification, and detection of nucleic acids. By making use of multiplex fluorescence detection, multiple target species may be detected and analyzed in parallel.

For real-time PCR, fluorescence is used to measure the amount of amplification in one of three general techniques. The first technique is the use of a dye, such as Sybr Green (Molecular Probes, Eugene, Oreg.), whose fluorescence increases upon binding to double-stranded DNA. The second technique uses fluorescently labeled probes whose fluorescence changes when bound to the amplified target sequence (hybridization probes, hairpin probes, etc.). This technique is similar to using a double-stranded DNA binding dye, but is more specific because the probe will bind only to a certain section of the target sequence. The third technique is the use of hydrolysis probes (Taqman™, Applera BioSystems, Foster City Calif.), in which the exonuclease activity of the polymerase enzyme cleaves a quencher molecule from the probe during the extension phase of PCR, making it fluorescently active.

In each of the approaches, fluorescence is linearly proportional to the amplified target concentration. Data acquisition system 21 measures an output signal from detector 18 (or alternatively optionally sampled and communicated by control unit 23) during the PCR reaction to observe the amplification in near real-time. In multiplex PCR, the multiple targets are labeled with different dyes that are measured independently. Generally speaking, each dye will have different absorbance and emission spectra. For this reason, optical modules 16 may have excitation sources, lenses and related filters that are optically selected for interrogation of sample 22 at different wavelengths.

Some examples of suitable construction techniques or materials that may be adapted for use in connection with the present invention may be described in, e.g., commonly-assigned U.S. Pat. No. 6,734,401 titled "ENHANCED SAMPLE PROCESSING DEVICES SYSTEMS AND METHODS" (Bedingham et al.) and U.S. Patent Application Publication No. US 2002/0064885 titled "SAMPLE PROCESSING DEVICES." Other useable device constructions may be found in, e.g., U.S. Provisional Patent Application Ser. No. 60/214,508 filed on Jun. 28, 2000 and entitled "THERMAL PROCESSING DEVICES AND METHODS"; U.S. Provisional Patent Application Ser. No. 60/214,642 filed on Jun. 28, 2000 and entitled "SAMPLE PROCESSING DEVICES, SYSTEMS AND METHODS"; U.S. Provisional Patent Application Ser. No. 60/237,072 filed on Oct. 2, 2000 and entitled "SAMPLE PROCESSING DEVICES, SYSTEMS AND METHODS"; U.S. Provisional Patent Application Ser. No. 60/260,063 filed on Jan. 6, 2001 and titled "SAMPLE PROCESSING DEVICES, SYSTEMS AND METHODS"; U.S. Provisional Patent Application Ser. No. 60/284,637 filed on Apr. 18, 2001 and titled "ENHANCED SAMPLE PROCESSING DEVICES, SYSTEMS AND METHODS"; and U.S. Patent Application Publication No. US 2002/0048533 titled "SAMPLE PROCESSING DEVICES AND CARRIERS." Other potential device constructions may be found in, e.g., U.S. Pat. No. 6,627,159 titled "CENTRIFUGAL FILLING OF SAMPLE PROCESSING DEVICES" (Bedingham et al.). The entire content of these disclosures are incorporated herein by reference.

Figure 2:
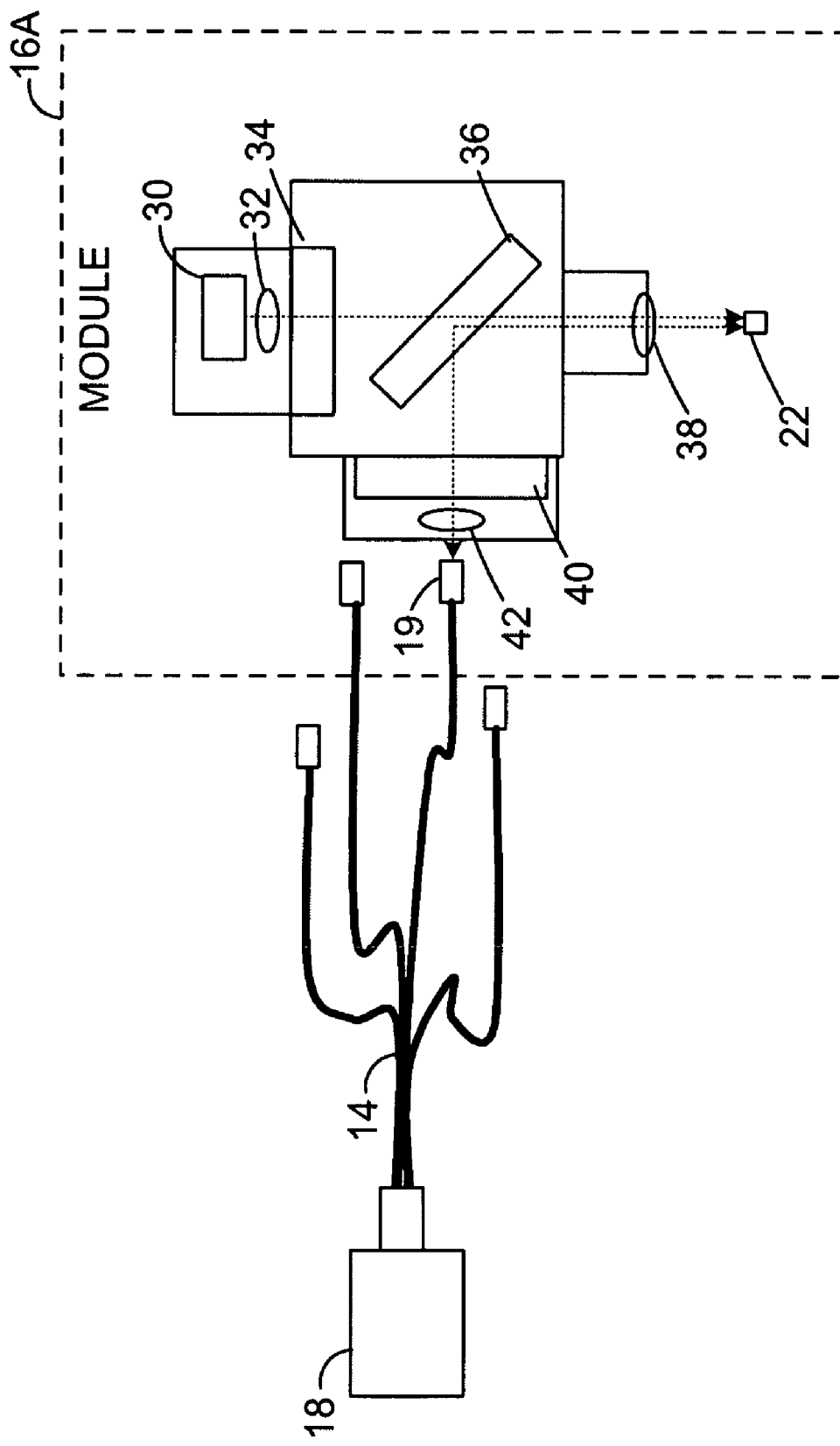
FIG. 2 is a schematic diagram illustrating an exemplary optical module, which may correspond to any of a plurality of optical modules of the fluorescence detection device of FIG. 1.

FIG. 2 is a schematic diagram illustrating an exemplary optical module 16A, which may correspond to any of optical modules 16 of FIG. 1. In this example, optical module 16A contains a high-power excitation source, LED 30, a collimating lens 32, an excitation filter 34, a dichroic filter 36, a focusing lens 38, a detection filter 40, and a lens 42 to focus the fluorescence into optical output port 19 coupled to one leg of fiber optic bundle 14.

Consequently, the excitation light from LED 30 is collimated by collimating lens 32, filtered by excitation filter 34, transmitted through dichroic filter 36, and focused into the sample 22 by focusing lens 38. The resulting fluorescence emitted by the sample is collected by the same focusing lens 38, reflected off of dichroic filter 36, and filtered by detection filter 40 before focused into one leg of fiber optic bundle 14 coupled to optical output port 19. The optic bundle 14 then transfers the light to detector 18.

LED 30, collimating lens 32, excitation filter 34, dichroic filter 36, focusing lens 38, detection filter 40, and lens 42 are selected based on the specific absorption and emission bands of the multiplex dye with which optical module 16A is to be used. In this manner, multiple optical modules 16 may be configured and loaded within device 10 to target different dyes.

Table 1 lists exemplary components that may be used in a 4-channel multiplex fluorescence detection device 10 for a variety of fluorescent dyes. FAM, HEX, JOE, VIC, TET, ROX are trademarks of Applera, Norwalk, Calif. Tamra is a trademark of AnaSpec, San Jose, Calif. Texas Red is a trademark of Molecular Probes. Cy 5 is a trademark of Amersham, Buckinghamshire, United Kingdom.

TABLE 1

| Optical Module | LED | Excitation Filter | Detection Filter | Dye |
| --- | --- | --- | --- | --- |
| 1 | blue | 475 nm | 520 nm | FAM, Sybr Green |
| 2 | green | 530 nm | 555 nm | HEX, JOE, VIC, TET |
| 3 | orange | 580 nm | 610 nm | TAMRA, ROX, Texas Red |
| 4 | red | 630 nm | 670 nm | Cy 5 |

One advantage of the described modular, multiplex detection architecture is the flexibility in optimizing detection for a wide variety of dyes. Conceivably a user may have a bank of several different optical modules that can be plugged into device 10 as needed, of which N can used at any one time, where N is the maximum number of channels supported by the device. Therefore, device 10 and optical modules 16 may be used with any fluorescent dye and PCR detection method. A larger fiber optic bundle may be used to support a larger number of detection channels. Moreover, multiple fiber optic bundles may be used with multiple detectors. For example, two 4-legged fiber optic bundles may be used with eight optical modules 16 and two detectors 18.

Figure 3:
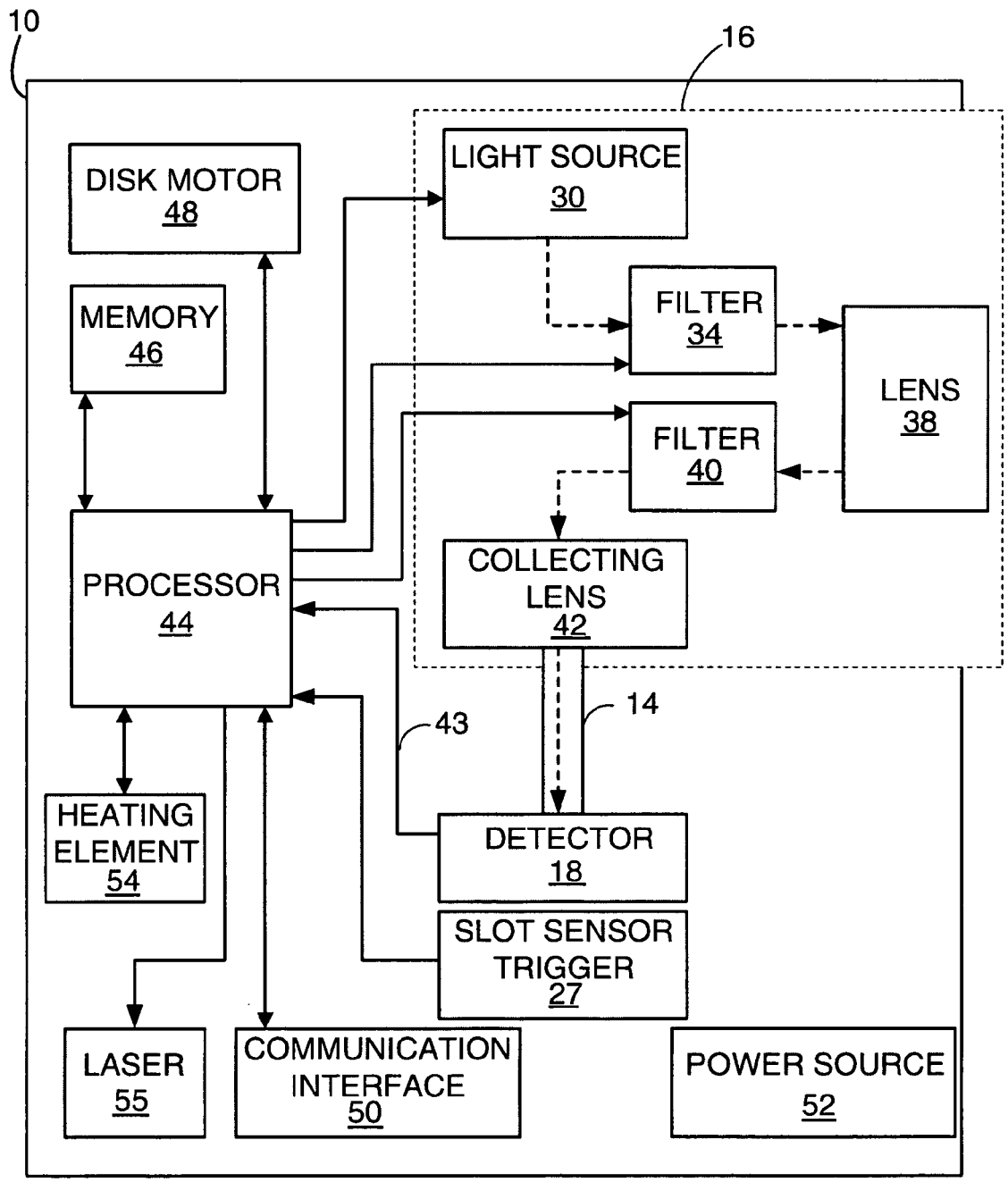
FIG. 3 is a block diagram illustrating an example embodiment of the multiplex fluorescence detection device in further detail.

FIG. 3 is a functional block diagram of the multiplex fluorescence detection device 10. In particular, FIG. 3 indicates the electrical connections between device components and the general paths of light through the components. In the example of FIG. 3, device 10 includes at least one processor 44 or other control logic, memory 46, disk motor 48, light source 30, excitation filter 34, lens 38, detection filter 40, collecting lens 42, detector 18, slot sensor trigger 27, communication interface 50, heating element 54, laser 55 and power source 52. As shown in FIG. 3, lens 38 and collecting lens 42 need not be electrically connected to another component. Further, light source 30, filters 34 and 40, lens 38 and collecting lens 42 are representative of one optical module 16. Although not illustrated in FIG. 3, device 10 may contain additional optical modules 16, as described previously. In that case, each additional optical module may include components arranged substantially similarly as to those shown in FIG. 3.

Light follows a certain path through several components in FIG. 3. Once light is emitted by light source 30, it enters excitation filter 34 and leaves as light of a discrete wavelength. It then passes through lens 38 where it leaves detection device 10 and excites sample 22 within a process chamber (not shown). Sample 22 responds by fluorescing at a different wavelength, at which time this light enters lens 38 and is filtered by detection filter 40. Filter 40 removes background light of wavelengths outside of the desired fluorescence from sample 22. The remaining light is sent through collecting lens 42 and enters a leg of fiber optic bundle 14 before being detected by detector 18. Detector 18 subsequently amplifies the received light signal.

Processor 44, memory 46 and communication interface 50 may be part of control unit 23. Processor 44 controls disk motor 48 to rotate or spin disk 13 as needed to collect fluorescence information or move fluid through disk 13. Processor 44 may use disk position information received from slot sensor trigger 27 to identify the location of chambers on disk 13 during rotation and synchronize the acquisition of florescence data received from the disk.

Processor 44 may also control when the light source 30 within optical module 16 is powered on and off. In some embodiments, processor 44 controls excitation filter 34 and detection filter 40. Depending on the sample being illuminated, processor 44 may change the filter to allow a different wavelength of excitation light to reach the sample or a different wavelength of fluorescence to reach collecting lens 42. In some embodiments, one or both filters may be optimized for the light source 30 of the particular optical module 16 and not changeable by processor 44.

Collecting lens 42 is coupled to one leg of fiber bundle 14 that provides an optical path for the light from the collecting lens to detector 18. Processor 44 may control the operation of detector 18. While detector 18 may constantly be detecting all light, some embodiments many utilize other acquisition modes. Processor 44 may determine when detector 18 collects data and may programmatically set other configuration parameters of detector 18. In one embodiment, detector 18 is a photomultiplier tube that captures fluorescence from light provided by collecting lens 42. In response, detector 18 produces an output signal 43 (e.g., an analog output signal) representative of the received light. Although not shown in FIG. 3, detector 18 may concurrently receive light from other optical modules 16 of device 10. In that case, output signal 19 electrically represents a combination of the optical input received by detector 18 from the various optical modules 16.

Processor 44 may also control data flow from device 10. Data such as sampled fluorescence from detector 18, temperature of the samples from heating element 54 and related sensors, and disk rotation information may be stored into memory 46 for analysis. Processor 44 may comprise any one or more of a microprocessor, digital signal processor (DSP), application specific integrated circuit (ASIC), field-programmable gate array (FPGA), or other digital logic circuitry. Moreover, processor 44 provides an operating environment for firmware, software, or combinations thereof, stored on a computer-readable medium, such as memory 46.

Memory 46 may include one or more memories for storing a variety of information. For example, one memory may contain specific configuration parameters, executable instructions, and one may contain collected data. Therefore, processor 44 may use data stored in memory 46 for controlling device operation and calibration. Memory 46 may include any one or more of a random access memory (RAM), read-only memory (ROM), electronically-erasable programmable ROM (EEPROM), flash memory, or the like.

Processor 44 may additionally control heating element 54. Based upon the instructions contained within memory 46, the heating element 54 may be selectively driven to control the temperature of one or more chambers according to desired heating profiles. Generally, heating element heats one radial section of disk 13 as the disk spins. Heating element 54 may comprise a halogen bulb and reflector for focusing heating energy on a specific area of disk 13. In other embodiments, heating element 54 may heat one or more chambers sequentially. This embodiment would require disk 13 to be stationary while a chamber is heated. In any embodiment, heating element 54 may be capable of turning on and off extremely quickly as needed.

Laser 55 is used to control valve opening which allows contents of an inner chamber to flow to another chamber on disk 13, e.g., a process chamber. Processor 44 and supporting hardware drives laser 55 to selectively open specific valves contained with disk 13. Processor 44 may interact with a laser sensor underneath disk 13 for determining the position of the laser relative to the desired valve. When in position, processor 44 outputs signals to direct laser 55 to produce a burst of energy targeted at the valve. In some cases, the burst may last for approximately 0.5 seconds, while other embodiments may include opening times of shorter or greater duration. A laser energy and pulse duration may be controlled by processor 44 through communication with laser 55.

Processor 44 utilizes communication interface 50 to communicate with data acquisition system 21. The communication interface 50 may include a single method or combination of methods to transfer data. Some methods may include a universal serial bus (USB) port or IEEE 1394 port for hardwire connectivity with high data transfer rates. In some embodiments, a storage device may be directly attached to one of these ports for data storage for post processing. The data may be pre-processed by processor 44 and ready for viewing, or the raw data may need to be completely processed before analyzing can begin.

Communications with detection device 10 may also be accomplished by radio frequency (RF) communication or a local area network (LAN) connection. Moreover, connectivity may be achieved by direct connection or through a network access point, such as a hub or router, which may support wired or wireless communications. For example detection device 10 may transmit data on a certain RF frequency for reception by the target data acquisition device 21. Data acquisition device 21 may be a general purpose computer, a notebook computer, a handheld computing device, or an application-specific device. Further, multiple data acquisition devices may receive the data simultaneously. In other embodiments, the data acquisition device 21 may be included with detection device 10 as one integrated detection and acquisition system.

In addition, detection device 10 may be able to download updated software, firmware, and calibration data from a remote device over a network, such as the internet. Communication interface 50 may also enable processor 44 to monitor inventory report any failures. If operational problems occur, processor 44 may be able to output error information to assist a user in trouble shooting the problems by providing operational data. For example, processor 44 may provide information to help the user diagnose a failing heating element or a synchronization problem.

Power source 52 delivers operating power to the components of device 10. Power source 52 may utilize electricity from a standard 115 Volt electrical outlet or include a battery and a power generation circuit to produce the operating power. In some embodiments, the battery may be rechargeable to allow extended operation. For example, device 10 may be portable to detection of biological samples in an emergency, such as a disaster area. Recharging may be accomplished through the 115 Volt electrical outlet. In other embodiments, traditional batteries may be used.

Figure 4:
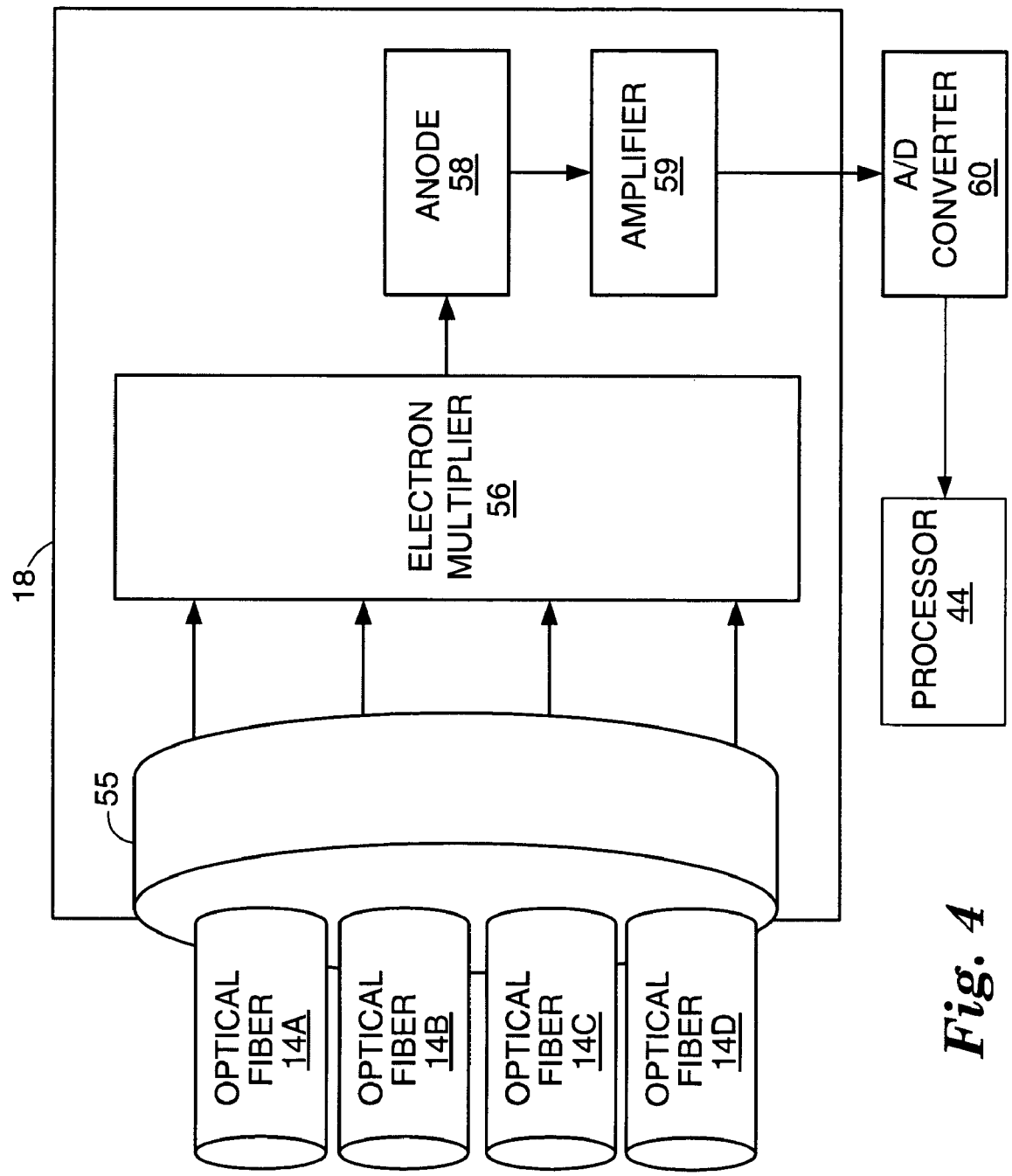
FIG. 4 is a block diagram of the a single detector coupled to four optical fibers of the optical fiber bundle.

FIG. 4 is a functional block diagram of the single detector 18 coupled to four optical fibers of the optical fiber bundle. In this embodiment, detector 18 is a photomultiplier tube. Each leg of fiber optic bundle 14, optical fiber 14A, optical fiber 14B, optical fiber 14C and optical fiber 14D, couples to an optical input interface 55 of detector 18. In this manner, light carried by any of optical fibers 14 is provided to a single optical input interface 55 of detector 18. In some embodiments, each leg of fiber optic bundle 14 may be of a different diameter, length, or both. For example, optical fiber 14A may be greater in diameter to transmit more light to detector 18 than the other optical fibers of fiber optic 14. The optical input interface 55 provides the aggregate light to electron multiplier 56. Anode 58 collects the electrons and produces a corresponding analog signal as output signal.

In other words, as shown, the optical fibers 14 fit within the input optical aperture for detector 18. Consequently, detector 18 may be used to detect light from each leg of optic bundle 14 simultaneously. Optical input interface 55 provides the light to electron multiplier 56. For a photomultiplier tube, the photons from the optical fibers first hit a photoemissive cathode, which in turn releases photoelectrons. The photoelectrons then cascade by hitting a series of dynodes, more photoelectrons being emitted upon contact with each dynode. The resulting group of electrons have essentially multiplied the small light signals originally transmitted by the optical fibers 14. The increased number of electrons finally are collected by anode 58. This current from anode 58 is transferred by a current to voltage amplifier 59 as an analog output signal which is representative of the optical florescent signals from the sample provided by the plurality of optical modules 16.

Control optical module 23 includes an analog to digital (A/D) converter 60 converts the analog signal to a stream of sampled digital data, i.e., a digital signal. Processor 44 receives the digital signal and stores the sampled data in memory 46 for communication to data acquisition device 21, as described in above. In some embodiments, A/D converter 60 may be contained within detector 18 instead of control optical module 23.

In this manner, a single detector 18 may be utilized to collect all light from the optic bundle 14 and produce a signal representative thereof. Once the signal is amplified by amplifier 59 and converted to a digital signal, it may be digitally separated into data corresponding to the light collected by each individual optical modules 16. The entire (i.e., aggregate) signal may be separated by frequency range into each detected signal representative of each fluorescence. These frequencies may be separated by a digital filter applied by data acquisition device 21 or within device 10.

In other embodiments, the amplified signal may be separated by frequency using analog filters and sent to separate channels before A/D converter 60. Each channel may then be separately digitized and sent to the data acquisition device. In either case, the single detector is able to capture all florescence information from each optical module 16. Data acquisition device 21 may then plot and analyze the signal acquired from each chamber of disk 13 in real-time without the need for multiple detectors.

In some embodiments, detector 18 may not be a photomultiplier tube. In general, detector 18 may be any type of analog or digital detection device capable of capturing light from multiple legs of an optical delivery mechanism, i.e., fiber bundle 14, and producing a transmittable representation of the captured light. Other embodiments may include a detector which is an amplified photodiode or a phototransistor.

Figure 5:
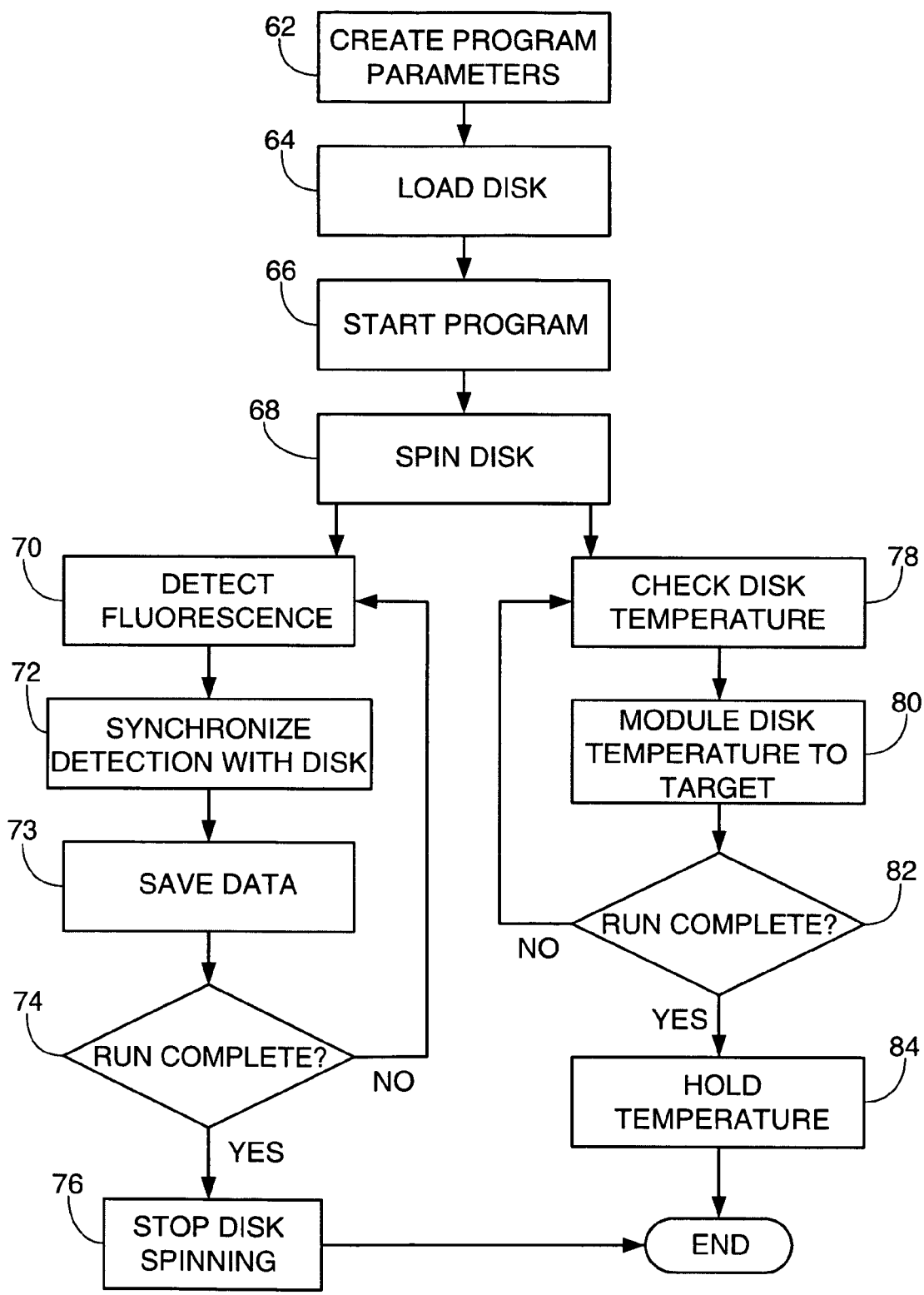
FIG. 5 is a flow diagram illustrating exemplary operation of the multiplex fluorescence detection device.

FIG. 5 is a flow diagram illustrating the operation of the multiplex fluorescence detection device 10. Initially, a user specifies program parameters on the data acquisition device 21 or via an interface with control unit 23 (62). For example, these parameters may include a velocity and time period for rotating disk 13, define temperature profiles for the reaction, and sample locations on disk 13.

Next, the user loads disk 13 into the detection device 10 (64). Upon securing the device 10, the user starts the program (66), causing control unit 23 to begin spinning the disk (68) at the specified rate. After the disk has begun to spin, two concurrent processes may occur.

First, the detection device 10 starts to detect fluorescence from the excitation light (70) produced by one or more reactions within one or more samples. The detector 18 amplifies the fluorescence signals from each sample, which are synchronized to each respective sample and time at which the fluorescence was emitted (72). During this process, processor 44 saves the captured data to memory 46 and may communicate the data to data acquisition device 10 in real-time to monitor the progress of the run and for additional processing (73). Alternatively, processor 44 may save the data within device 10 until the program is complete. The processor 44 continues to detect florescence of the samples and save data until the program is complete (74). Once the run is complete, control unit 23 stops the disk from spinning (76).

During this process, control unit 23 monitors the disk temperature (78) and modulates the disk, or each sample, temperature to attain the target temperature for that time (80). The control unit 23 continues to monitor and control the temperatures until the program is complete (82). Once the run is complete, control unit 23 holds the temperature of the samples to a target storage temperature, usually 4 degrees Celsius (84).

The operation of device 10 may vary from the example of FIG. 5. For example, the disk revolutions per minute may be modified throughout the program, and laser 55 may be utilized to open valves between chambers on the disk to allow for multiple reactions. These steps may occur in any order within the operation, depending on the program the user defines.

EXAMPLE

Figure 6:
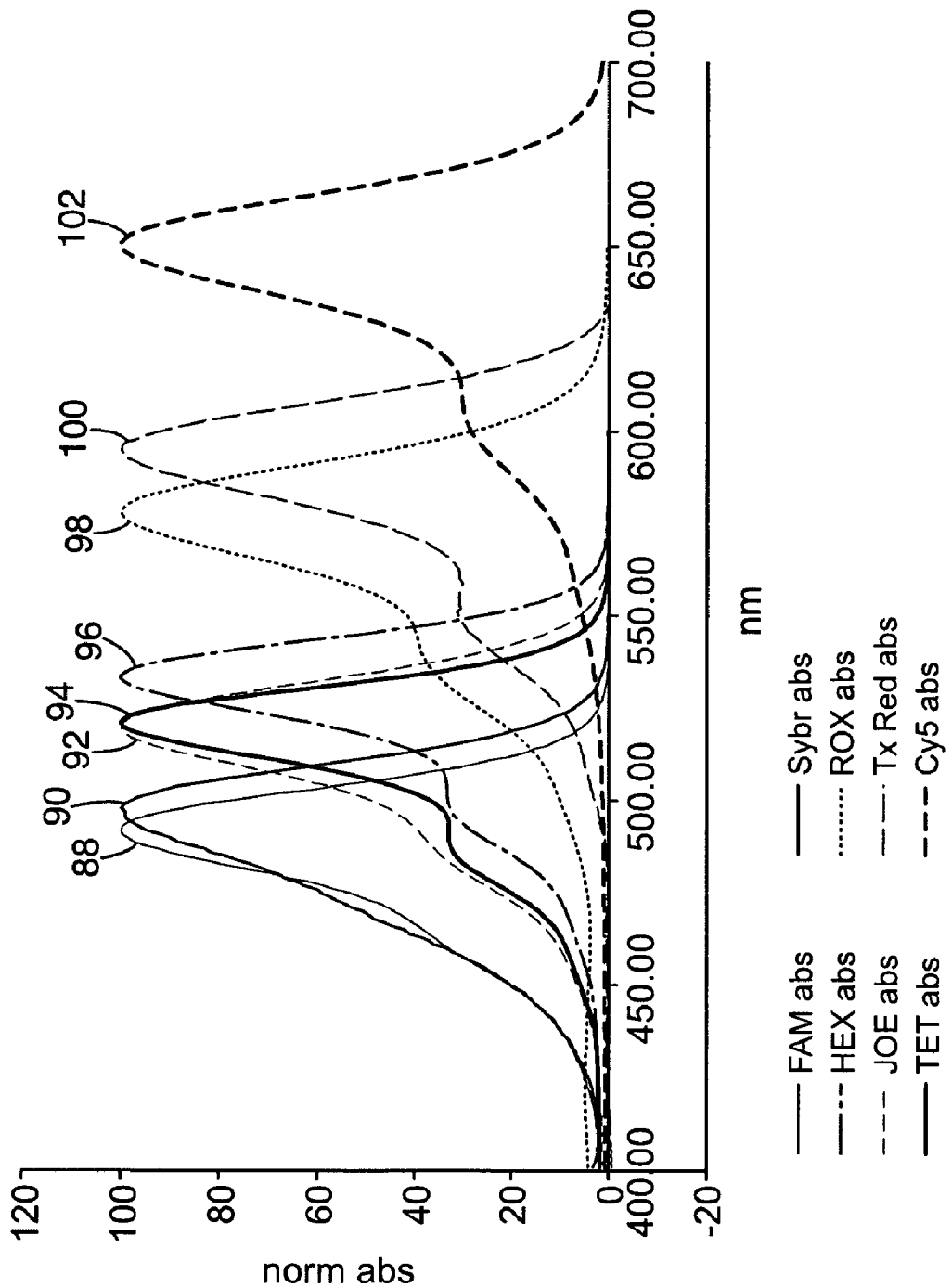
FIGS. 6 and 7 show the absorption and emission spectra of commonly used fluorescent dyes that may be utilized for multiplex PCR.
Figure 7:
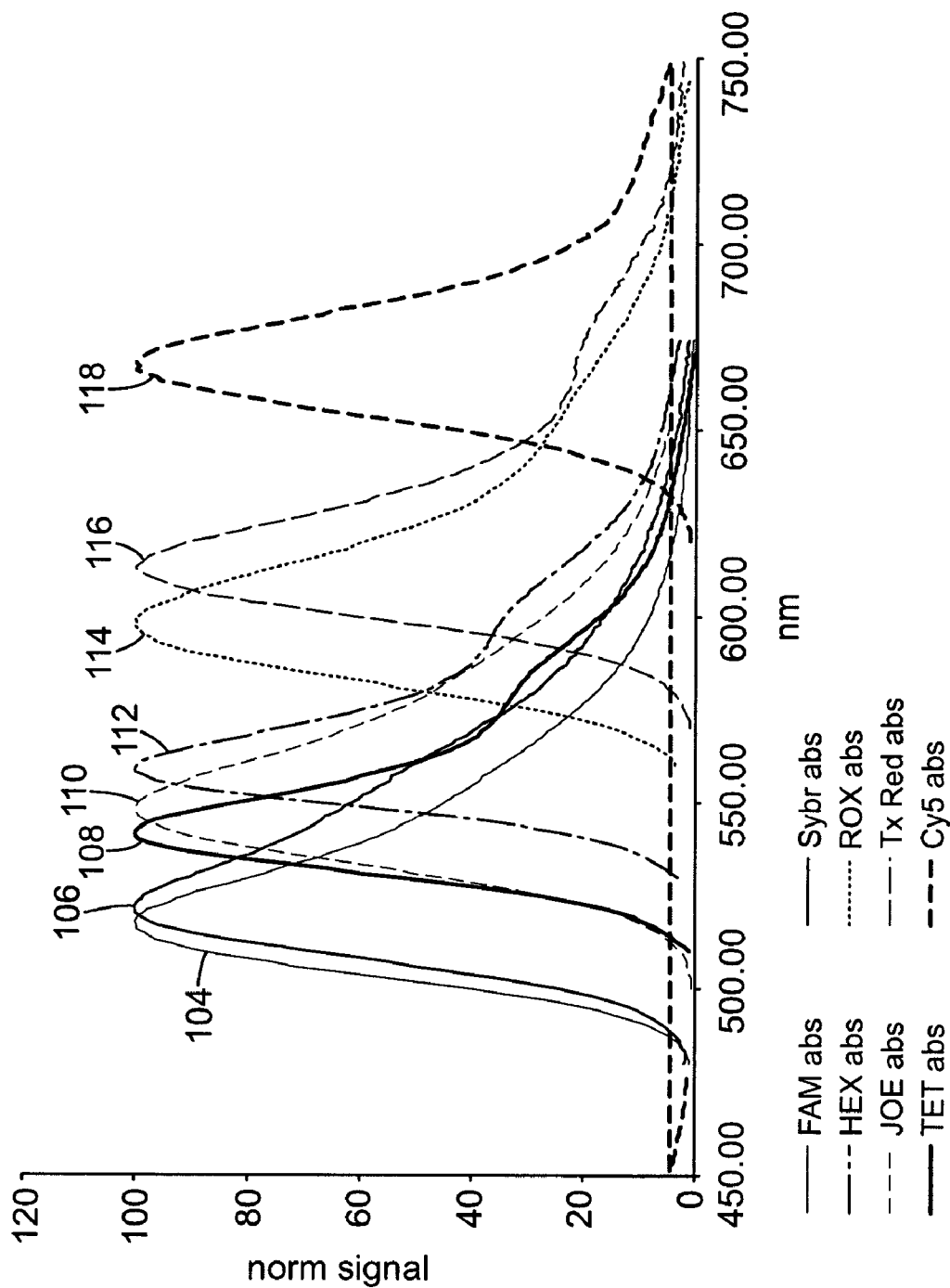

FIGS. 6 and 7 show the absorption and emission spectra of commonly used fluorescent dyes that may be utilized with device 10 for multiplex PCR. In these examples, the absorption maxima of the dyes vary from 480-620 nm, and the resulting emission maxima vary from 520-670 nm. The signals for each dye in FIG. 6 are numbered as FAM 88, Sybr 90, JOE 92, TET 94, HEX 96, ROX 98, Tx Red 100, and Cy5 102. The signals in FIG. 7 are FAM 104, Sybr 106, TET 108, JOE 110, HEX 112, ROX 114, Tx Red 116, and Cy5 118. FAM, HEX, JOE, VIC, TET, ROX are trademarks of Applera, Norwalk, Calif. Tamra is a trademark of AnaSpec, San Jose, Calif. Texas Red is a trademark of Molecular Probes. Cy 5 is a trademark of Amersham, Buckinghamshire, United Kingdom.

In one example, a 96 chamber disk was filled with different concentrations of FAM and ROX dye diluted in standard PCR reaction buffer. Four replicates of each dye were added in a 2× dilution series, starting from 200 nM FAM and 2000 nM ROX. Each sample volume was 10 µL. Chamber 82 had a mixture of 5 µL of 200 nM FAM and 5 µL of 2000 nM ROX. Device 10 was constructed as a two-channel multiplex PCR detection device having two optical modules 16 for detection of the dyes.

The first optical module (the FAM optical module) contained a blue LED, 475 nm excitation filter and a 520 nm detection filter. The second optical module (the ROX optical module) contained a green LED with a 560 nm excitation filter and a 610 nm detection filter. Another option would be to incorporate an orange LED and an excitation filter at 580 nm to optimize for ROX detection.

A PCR analysis was conducted, and fluorescent signals from the samples were multiplexed into a bifurcated fiber optic bundle. The fiber bundle was interfaced with a single detector, specifically a photomultiplier tube (PMT). Data was collected by a National Instruments data acquisition (DAQ) board interfaced with a Visual Basic data acquisition program executing on a general-purpose computer. Data was acquired while the disk was spinning at 1000 revolutions per minute (nominally). The FAM optical module and the ROX optical module were sequentially used to interrogate the samples. Each scan consisted of an average of 50 rotations. The raw data from the two optical modules is shown in FIGS. 8A and 8B.

Figure 8A:
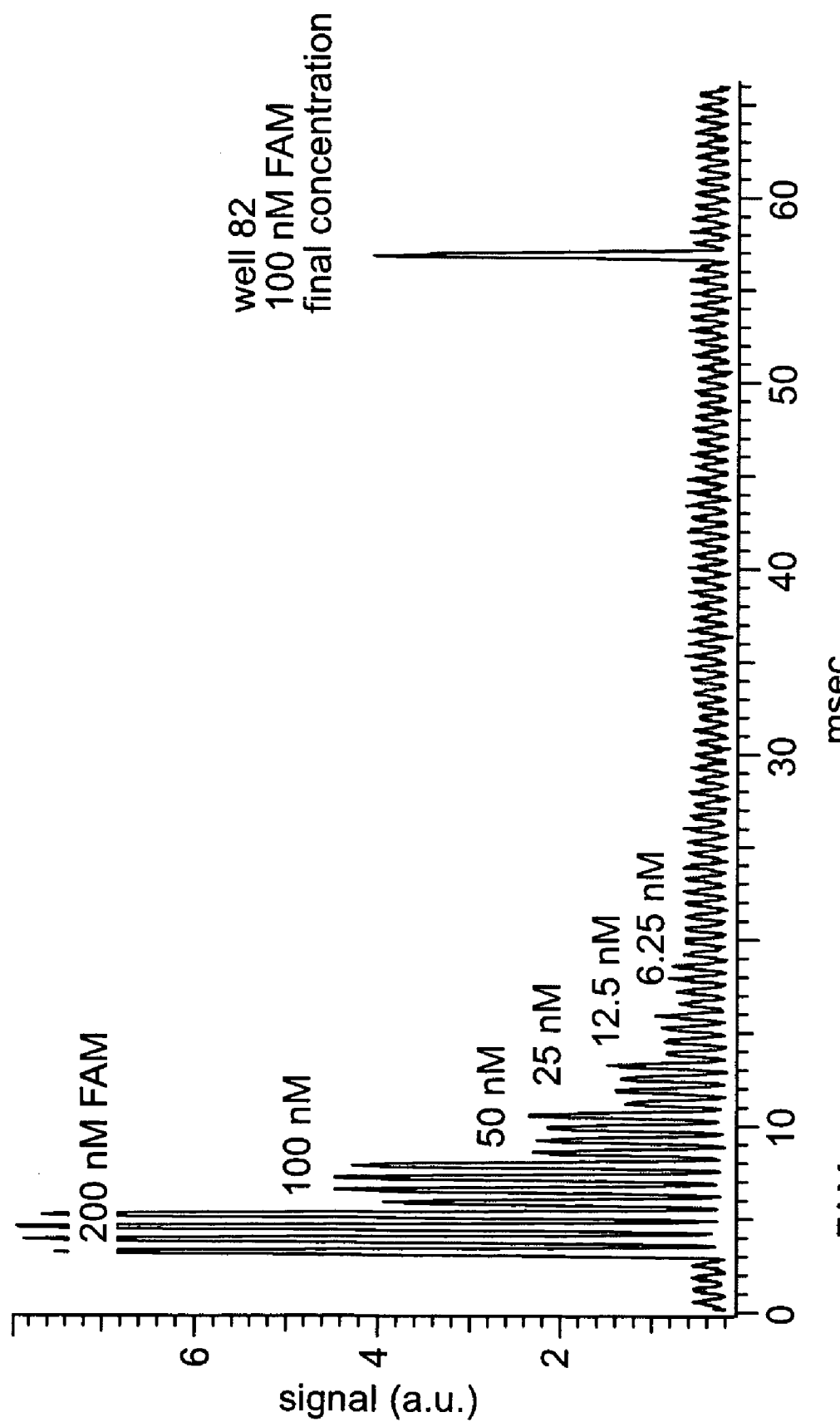
FIGS. 8A and 8B illustrate raw data acquired from two exemplary optical modules with a single detector during a PCR analysis.
Figure 8B:
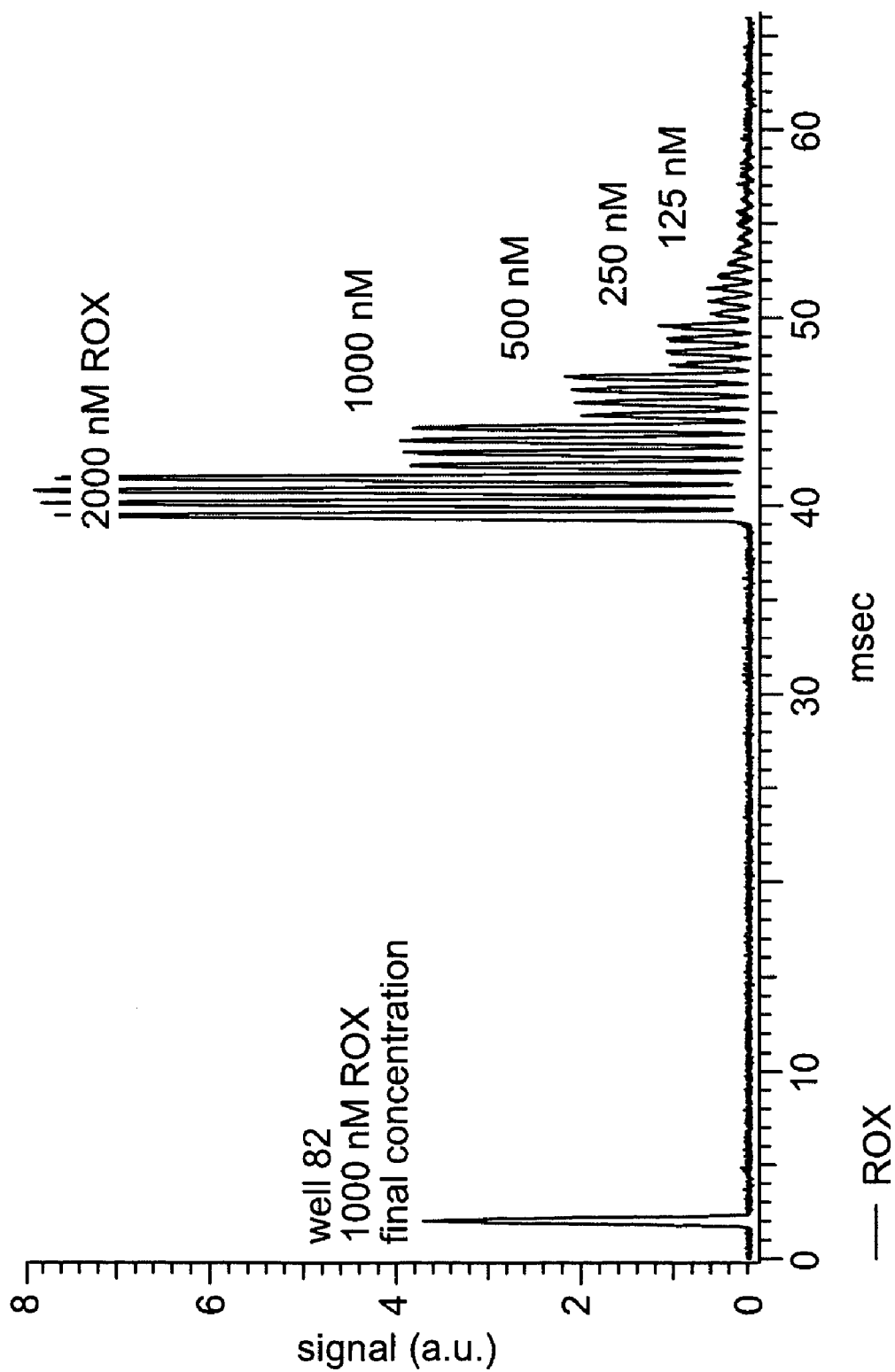

The graph in FIG. 8A was acquired by powering the LED in the FAM optical module, and the graph in 8B was acquired by powering the LED in the ROX optical module.

During the analysis, the collected data clearly showed that there was a time offset associated with optical modules being physically located over different chambers at any one time. An offset value was calculated by determining the time offset between optical modules 1 and 2 for a particular chamber, i.e., chamber 82 in this case. In other words, the time offset indicates the amount of time delay between data captured by the FAM optical module and data captured by the ROX optical module for the same chamber.

Figure 9:
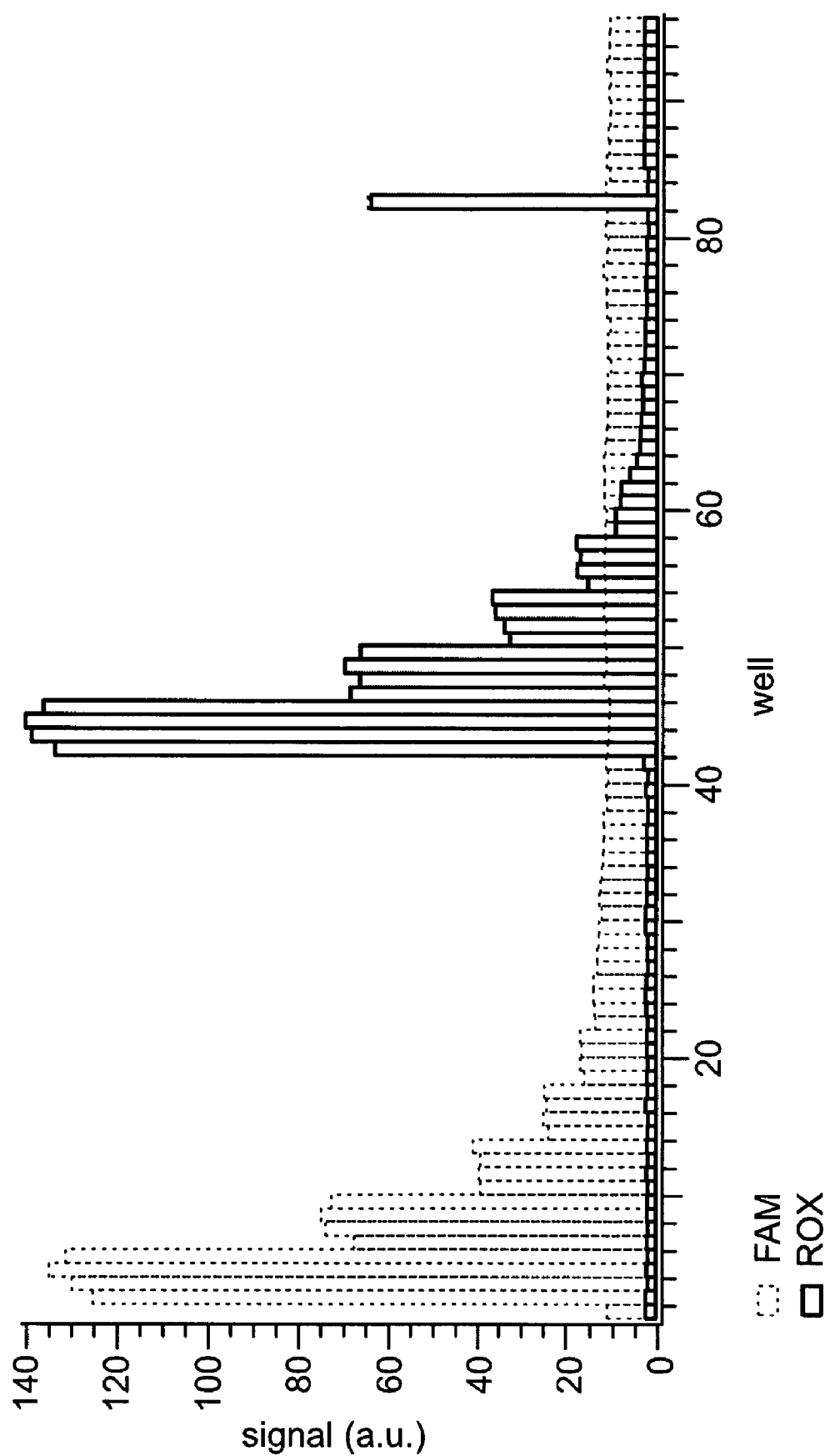
FIG. 9 is a graph that shows the data once adjusted for a time offset.

FIG. 9 is a graph that shows the offset-subtracted integrated data for each chamber. FAM is indicated by hash marked bars, ROX is indicated by open bars, and the ROX data is placed over the FAM data. The data showed that there was no signal from the ROX dye on optical module 1 and no signal from the FAM dye on optical module 2. There was a higher background on optical module 1, which may be rectified by using an optimized set of filters. The data was analyzed to determine the limit of detection (LOD), described as the signal equivalent to the baseline noise level. The baseline noise level was defined as the average of ten scans of a blank chamber plus 3 times the standard deviation.

Figure 10A:
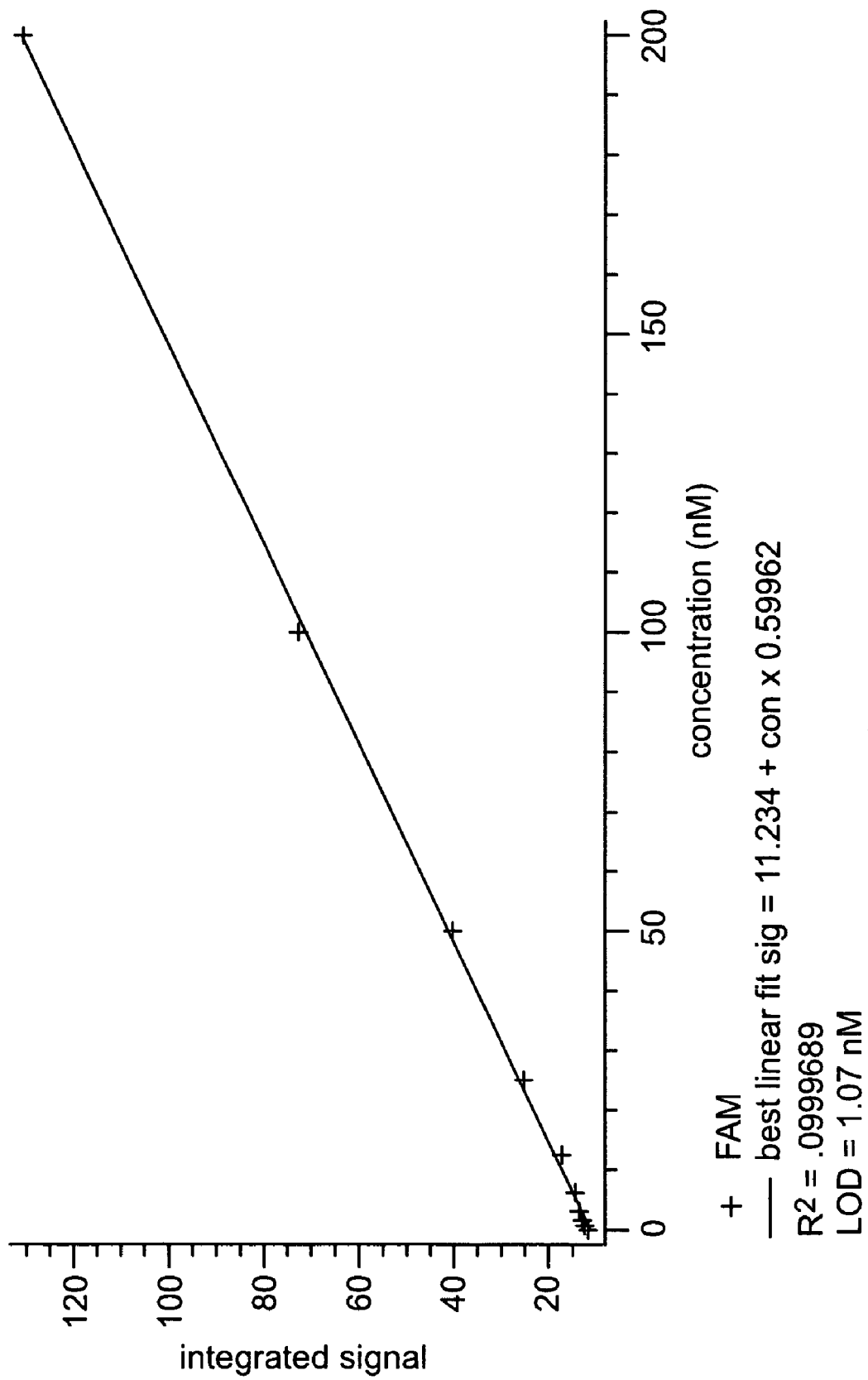
FIGS. 10A and 10B show a limit of detection (LOD) for the data received from two exemplary optical modules.
Figure 10B:
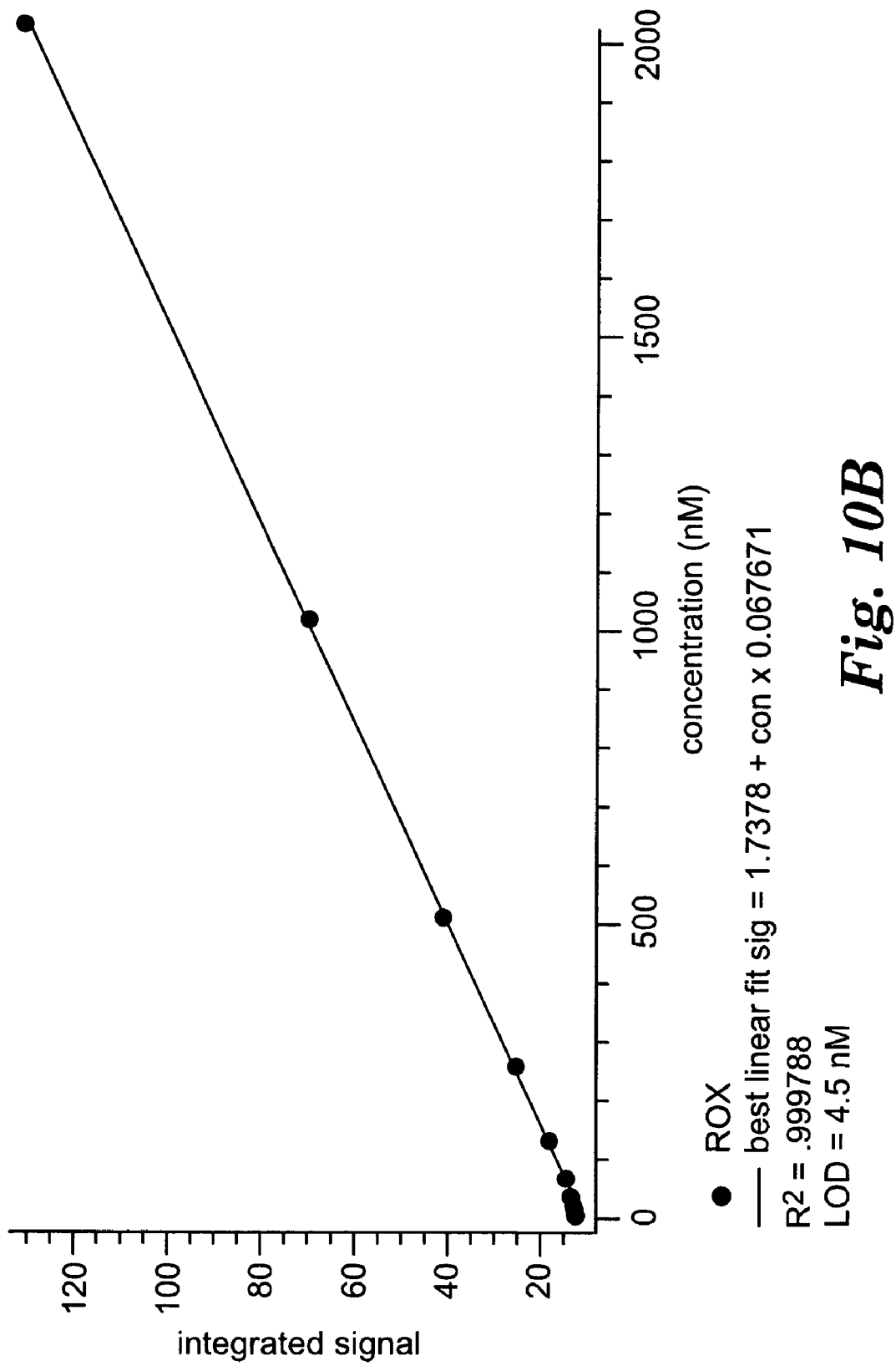

The LOD was determined by a linear least squares fit of the integrated signal plotted against the concentration of the FAM and ROX standards. The LOD of the FAM and ROX optical modules were calculated to be 1 and 4 nM, respectively, as shown in FIGS. 10A and 10B.

Various embodiments of the invention have been described. These and other embodiments are within the scope of the following claims.

The invention claimed is:

1. A detection device comprising:
   a motor to rotate a disk having a plurality of process chambers each holding a respective sample and a plurality of fluorescent dyes;
   a plurality of optical modules, wherein each of the optical modules includes a light source selected for a different one of the dyes and a lens to capture fluorescent light emitted from the disk;
   a detector; and
   a fiber optic bundle coupled to the plurality of optical modules to convey the fluorescent light from the multiple optical modules to the detector.

2. The detection device of claim 1, wherein each of the optical modules further comprises an excitation filter and a detection filter.

3. The detection device of claim 1, further comprising a slot sensor trigger that provides an output signal for synchronization of rotation of the disk with data provided by the detector.

4. The detection device of claim 1, wherein the fiber optic bundle includes a plurality of fiber optic legs that each terminate at the aperture of the detector.

5. The detection device of claim 1, wherein the detector comprises a photomultiplier, an amplified photodiode, an avalanche photodiode or a phototransistor.

6. The detection device of claim 1, wherein the light sources of the optical modules comprise light emitting diodes or laser diodes.

7. The detection device of claim 1, wherein the device includes at least two optical modules.

8. The detection device of claim 1, wherein the device includes at least four optical modules.

9. The detection device of claim 1, wherein the light sources are selected for detection of different species of a polymerase chain reaction (PCR) utilizing fluorescence detection at multiple wavelengths.

10. A detection system comprising.
    a data acquisition device; and
    a detection device coupled to the data acquisition device, wherein the detection device comprises:
       a motor to rotate a disk having a plurality of process chambers each having a plurality of species that emit fluorescent light at different wavelengths;
       a plurality of optical modules, wherein each of the optical modules is optically configured to excite the species and capture fluorescent light emitted by the species at different wavelengths;
       a detector; and
       a fiber optic bundle coupled to the plurality of optical modules to convey the fluorescent light from the multiple optical modules to the detector.

11. The system of claim 10, wherein the data acquisition device computes a time offset between the optical modules and processes data from the detection device based on the time offset.

12. The system of claim 10, wherein each of the optical modules further comprises an excitation filter and a detection filter selected for the different wavelengths.

13. The system of claim 10, wherein the detection device further comprises a slot sensor trigger that provides an output signal for synchronization of rotation of the disk with data provided by the detector.

14. The system of claim 13,
    wherein each optical module can be physically mounted within respective locations of the device, and
    wherein each optical module includes can be inserted within the respective location along guides that mate with one or more marking of the optical module.

15. The system of claim 14, wherein each optical module includes an optical output port for coupling to a leg of fiber optic bundle.

16. The system of claim 15, wherein the optical output port has a threaded end to couple to a threaded connector of the leg.

17. The system of claim 15, wherein the optical output port has a slidable connection that allows the fiber optic bundle to be slidably engaged and disengaged from the optical output port.

18. The system of claim 17, further comprising a bias member associated with the slidable connection to force the fiber optic bundle against the optical output port.

19. The system of claim 14, wherein each optical module has one or more electrical contacts for electronically coupling a control unit when fully inserted into the location.

20. The system of claim 10, wherein the fiber optic bundle includes a plurality of fiber optic legs that each terminate at the aperture of the detector.

21. The system of claim 10, wherein the detector is a photomultiplier, an amplified photodiode, an avalanche photodiode or a phototransistor.

22. A method comprising:
rotating a disk having a plurality of process chambers each having a plurality of species that emit fluorescent light at different wavelengths;
exciting the disk with a plurality of light beams to produce a plurality of emitted fluorescent light beams;
capturing the fluorescent light beams with a plurality of different optical modules, wherein the optical modules are optically configured for the different wavelengths;
conveying the fluorescent light beams from the plurality of optical modules to a single detector with a fiber optic bundle; and
outputting a signal from the detector representative of the detected light beams.

23. The method of claim 22, wherein exciting the disk with a plurality of light beams may be accomplished by sending the light beams through an excitation filter and capturing the fluorescent light beams may be accomplished by sending the fluorescent light beams through a detection filter.

24. The method of claim 22, further comprising providing an output signal from a slot sensor trigger for synchronization of rotation of the disk with data provided by the detector.

25. The method of claim 22, wherein the single detector comprises a photomultiplier, an amplified photodiode or a photothermistor.

26. The method of claim 22, wherein the plurality of light beams are produced by light emitting diodes or laser diodes.

27. The method of claim 22, wherein light beams are produced and captured from at least two optical modules.

28. The method of claim 22, wherein light beams are produced and captured from at least four optical modules.

29. The method of claim 22, further comprising selecting a wavelength for each of the plurality of light beams for exciting the different species of a polymerase chain reaction (PCR) utilizing fluorescence detection at multiple wavelengths.

* * * * *

UNITED STATES PATENT AND TRADEMARK OFFICE
CERTIFICATE OF CORRECTION

| | |
|---|---|
| PATENT NO. | : 7,709,249 B2 |
| APPLICATION NO. | : 11/174755 |
| DATED | : May 4, 2010 |
| INVENTOR(S) | : William Bedingham |

It is certified that error appears in the above-identified patent and that said Letters Patent is hereby corrected as shown below:

Column 14
Line 15, In Claim 10, delete "comprising." and insert -- comprising: --, therefor.

Signed and Sealed this

Tenth Day of August, 2010

David J. Kappos
*Director of the United States Patent and Trademark Office*